(12) United States Patent
Kim

(10) Patent No.: US 9,006,452 B2
(45) Date of Patent: Apr. 14, 2015

(54) METHOD FOR IMAGING ZINC ACTIVATION WITHIN A MITOCHONDRION USING A TWO-PHOTON FLUORESCENT PROBE, AND METHOD FOR MANUFACTURING THE TWO-PHOTON FLUORESCENT PROBE

(75) Inventor: Hwan Myung Kim, Gyeonggi-do (KR)

(73) Assignee: AJOU University Industry-Academic Cooperation Foundation, Gyeonggi-do (KR)

( * ) Notice: Subject to any disclaimer, the term of this patent is extended or adjusted under 35 U.S.C. 154(b) by 0 days.

(21) Appl. No.: 13/980,946

(22) PCT Filed: Oct. 18, 2011

(86) PCT No.: PCT/KR2011/007750
§ 371 (c)(1),
(2), (4) Date: Jul. 22, 2013

(87) PCT Pub. No.: WO2012/099317
PCT Pub. Date: Jul. 26, 2012

(65) Prior Publication Data
US 2013/0295599 A1    Nov. 7, 2013

(30) Foreign Application Priority Data
Jan. 21, 2011    (KR) ........................ 10-2011-0006521

(51) Int. Cl.
| | | |
|---|---|---|
| *C07F 9/6558* | (2006.01) | |
| *C07F 9/54* | (2006.01) | |
| *G01N 33/84* | (2006.01) | |
| *G01N 33/533* | (2006.01) | |
| *C07D 417/14* | (2006.01) | |

(52) U.S. Cl.
CPC ........... *C07F 9/65583* (2013.01); *C07F 9/5456* (2013.01); *G01N 33/84* (2013.01); *G01N 33/533* (2013.01); *C07D 417/14* (2013.01)

(58) Field of Classification Search
CPC .... C07F 9/65583; C07F 9/5456; G01N 33/84
See application file for complete search history.

(56) References Cited

FOREIGN PATENT DOCUMENTS

| | | |
|---|---|---|
| JP | 2009-084576 A | 4/2009 |
| KR | 10-0924999 B | 10/2009 |
| KR | 10-0954585 B | 4/2010 |

OTHER PUBLICATIONS

Masanta et al. "A Mitochondrial-Targeted Two-Photon Probe for Zinc Ion" Journal of the American Chemical Society, 2011, vol. 133, pp. 5698-5700.*
Kim, Hwan Myung et al.: "Two-Photon Fluorescent Turn-On Probe for Lipid Rafts in Live Cell and Tissue", *J. Am. Chem. Soc.*, 2008, 130, pp. 4246-4247.
Ono, Masahiro et al.: "Push-pull benzothiazole derivatives as probes for detecting β-amyloid plaques in Alzheimer's brains", *Bioorganic & Medicinal Chemistry*, 17 (2009, pp. 7002-7007.

* cited by examiner

*Primary Examiner* — Joseph Kosack
(74) *Attorney, Agent, or Firm* — Frommer Lawrence & Haug LLP; Ronald R. Santucci

(57) ABSTRACT

Provided is a two-photon fluorescent probe, and more particularly, a two-photon fluorescent probe which is one or more selected from compounds represented by Formulae 1 and 2, a method for manufacturing the same, and an imaging method of zinc ions within the mitochondrion using the same. Since two probes are introduced into one molecule, the two-photon fluorescent probe of the present invention can selectively dye the mitochondria, simultaneously with reacting with zinc ions, thereby generating intense fluorescence. Thus, the two-photon fluorescent probe of the present invention can be used for the imaging of zinc ion distribution and activation within the mitochondrion in living cells or intact biological tissues.

6 Claims, 6 Drawing Sheets

METHOD FOR IMAGING ZINC ACTIVATION WITHIN A MITOCHONDRION USING A TWO-PHOTON FLUORESCENT PROBE, AND METHOD FOR MANUFACTURING THE TWO-PHOTON FLUORESCENT PROBE

This application is a 371 of PCT/KR2011/007750 filed on Oct. 18, 2011, published on. Jul. 26, 2012 under publication number WO 2012/099317, which claims priority benefits from Korean Patent Application Number 10-2011-0006521 filed Jan. 21, 2011, the disclosure of which is incorporated herein by reference.

BACKGROUND (a) Technical Field

The present disclosure relates to a fluorescent probe which is selectively localized in mitochondria of a cell, an intracellular organelle. More particularly, the present disclosure relates to a two-photon fluorescent probe with high sensitivity and selectivity that can visualize the activation of zinc ions present inside the mitochondria by using a two-photon microscope in real time.

(b) Background Art

A change in the intracellular distribution of zinc ions is very important in studying physiological and pathological activities. In particular, zinc ions serve to regulate sensitivity of the central nervous system, the brain and play an important role in synaptic plasticity. For a proper brain function, it is essential to maintain homeostasis of an intracellular concentration of zinc ions. According to a recent study, it has been found that when the intracellular concentration of zinc ions becomes high, the mitochondria in cells absorb the zinc ions to help the cells maintain homeostasis of zinc ions. If the intracellular concentration of zinc ions loses balance, neurological diseases such as Alzheimer's and Parkinson's diseases may be caused.

To understand the biological roles of zinc ions, a variety of one-photon fluorescent probes derived from quinoline (TSQ, Zinquin, and TFLZn) and fluoroscein (FluZn-3, Znpyr, ZnAF, etc.) have been developed. However, most of such one-photon fluorescent probes are not selective to mitochondria and show poor selectivity to zinc ions.

Further, when a one-photon fluorescence probe is used, there is a common problem of using shorter excitation wavelengths (<500 nm). The short excitation wavelength may cause several problems including a shallow penetration depth (<100 μm), photo bleaching and self-fluorescence of cells, that limit the application for tissue imaging. To solve the problems, there has been proposed a two-photon microscope (TPM) employing a two-photon with low excitation energy. The two-photon microscope has several advantages that it requires low energy for excitation, enables to detect zinc ions in intact cells, and allows to observe biological phenomena in deeper tissues.

However, two-photon fluorescent probes that CaO selectively detect zinc ions present inside mitochondria of cells have not yet been developed.

The present inventors have endeavored to develop a fluorescent marker that can selectively detect zinc ions present inside the mitochondria and solve the problem of the conventional one-photon fluorescent probe with a short excitation wavelength, and therefore developed a two-photon fluorescent probe (SZn-Mito) capable of selectively detecting zinc ions present inside the mitochondria.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art.

In one aspect, the present invention provides a two-photon fluorescent probe (SZn-Mito) capable of selectively detecting zinc ions preset inside the mitochondria of cells, a representative intracellular organelle.

In an exemplary embodiment, the present invention provides a two-photon fluorescent probe (SZn-Mito) selected from compounds represented by following Formulae 1 and 2:

[Formula 1]

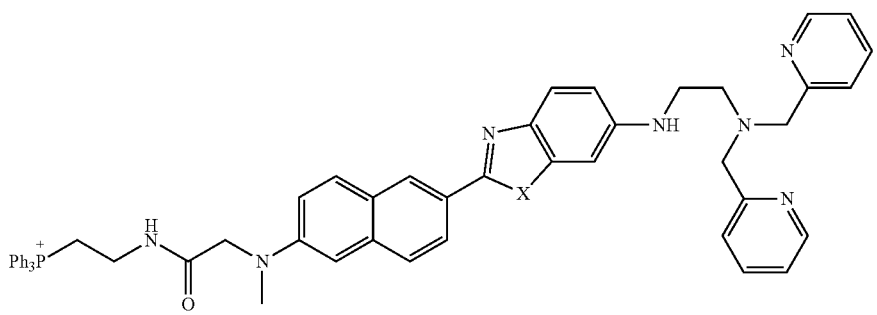

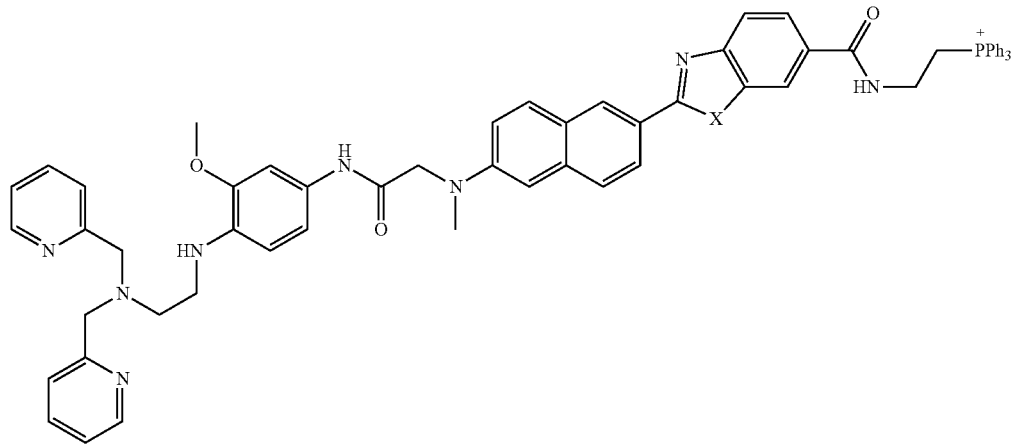

wherein X is S or O.

In another aspect, the present invention provides a method for manufacturing the above two-photon fluorescent probe (SZn-Mito).

In an exemplary embodiment, the present invention provides a method for manufacturing a two-photon fluorescent probe represented by following Formula 1 by reacting a compound represented by following Formula 3 with a compound represented by following Formula 4 under nitrogen atmosphere:

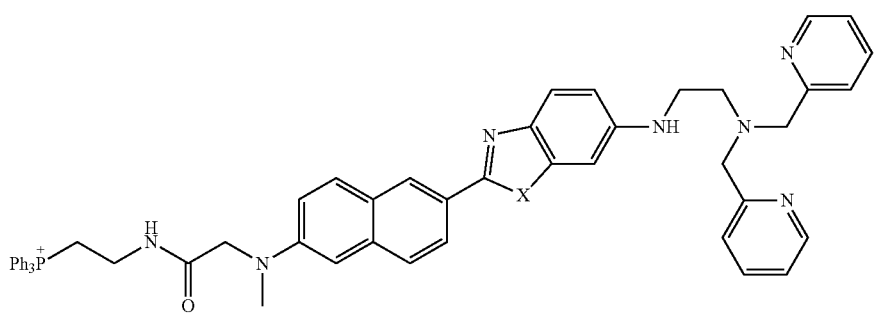

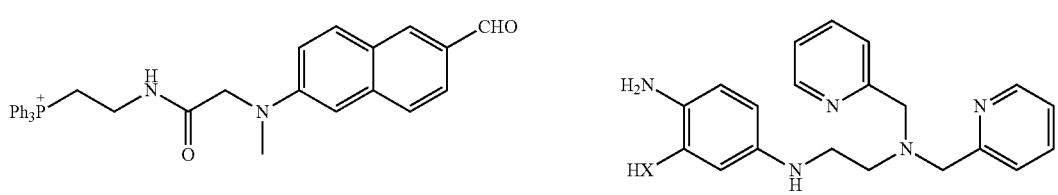

wherein X is S or O.

In another exemplary embodiment, the present invention provides a method for manufacturing a two-photon fluorescent probe represented by following Formula 2 by reacting a compound represented by following Formula 5 with a compound represented by following Formula 6 under nitrogen atmosphere.

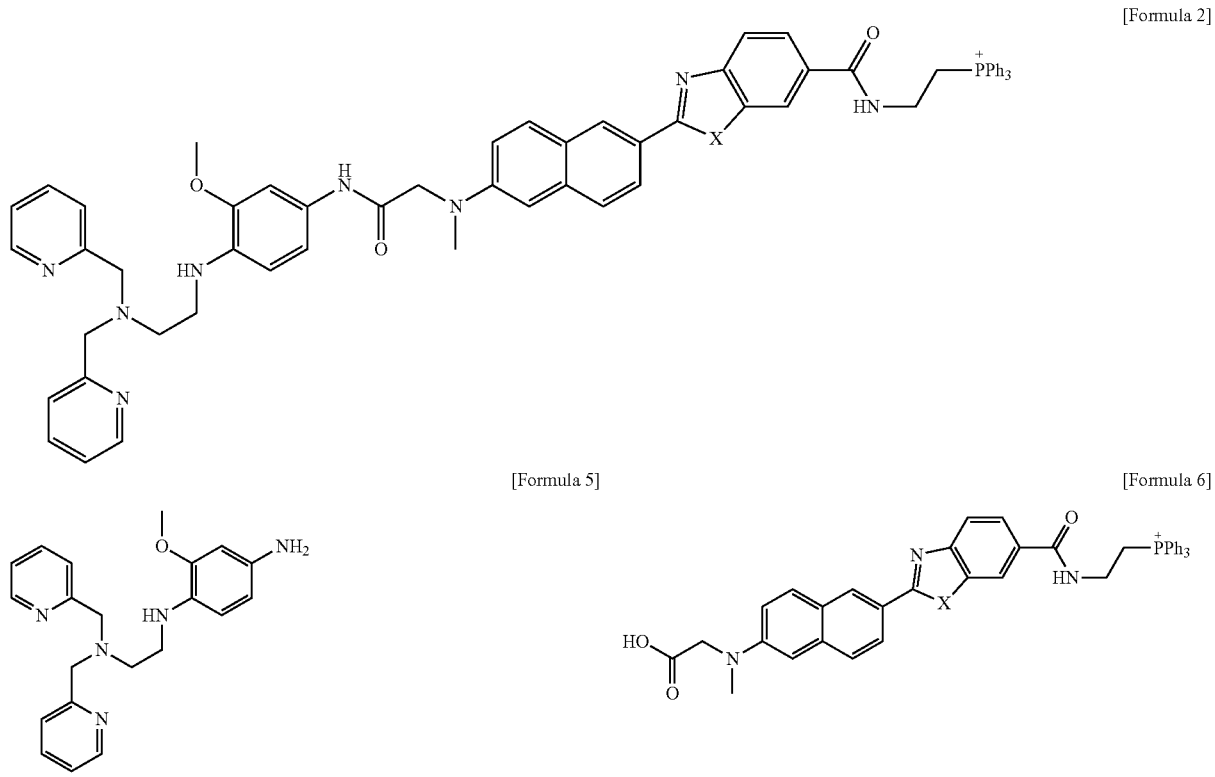

wherein X is S or O.

In still another aspect, the present invention provides an imaging method of free zinc ions present inside the mitochondria by using the above two-photon fluorescent probe (SZn-Mito).

In an exemplary embodiment, the present invention provides an imaging method of zinc ions present inside the mitochondria, including:

(a) injecting the two-photon fluorescent probe into cells;

(b) reacting the two-photon fluorescent probe with zinc ions within the mitochondria, thereby generating fluorescence; and (c) observing the fluorescence with a two-photon microscope.

Other aspects and exemplary embodiments of the invention are discussed infra.

The above and other features of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
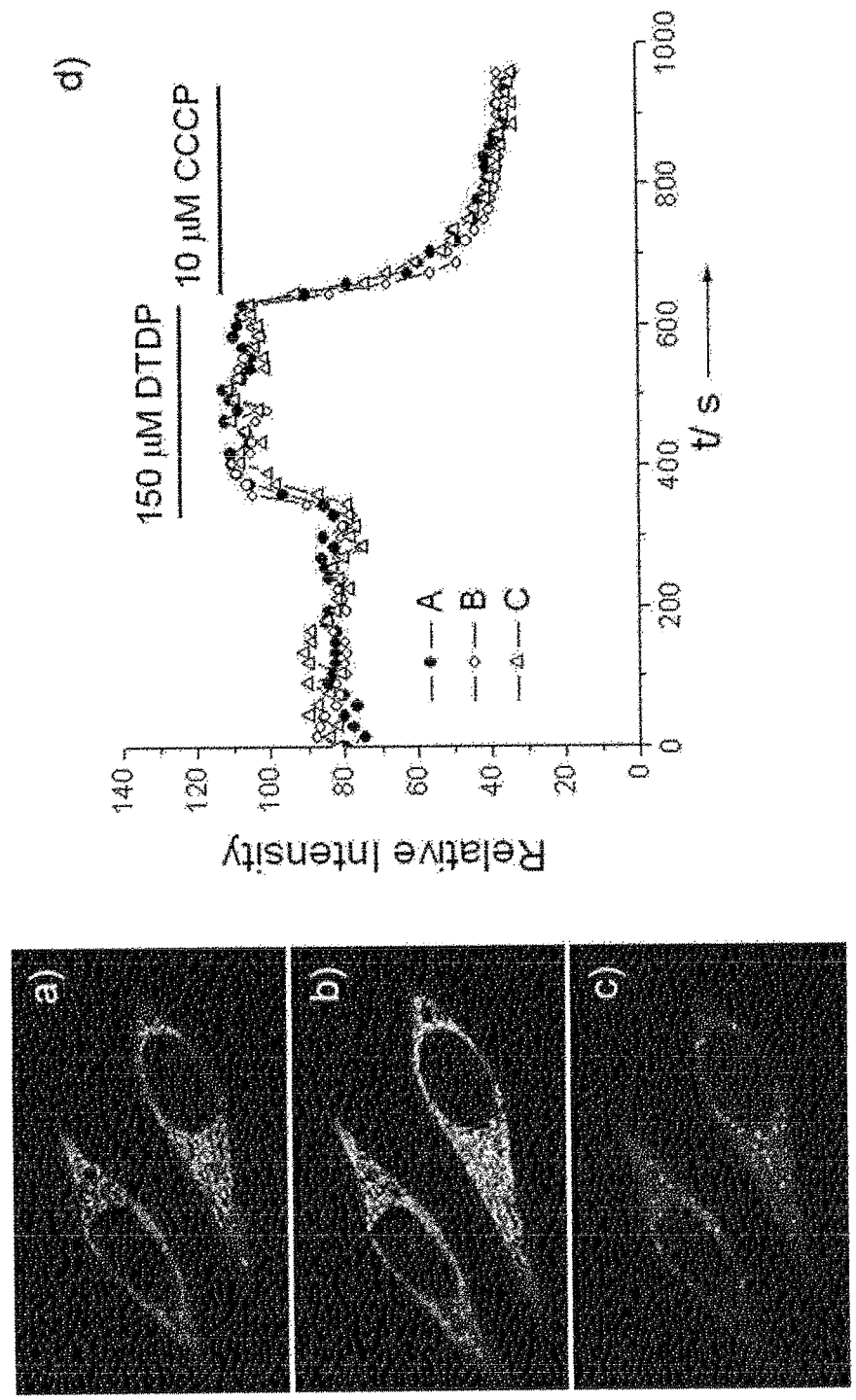
FIG. 1 shows images of HeLa cells labeled with a 0.5 two-photon fluorescent probe (SZn-Mito) observed under a two-photon microscope (TPM), in which (a) represents the image before labeling, (b) represents the image after the cells were labeled with 150 DTDP in an imaging solution, (c) represents the image after adding 10 CCCP to (b), and (d) represents relative TPEF intensity of the two-photon fluorescent probe (SZn-Mito)-labeled HeLa cells as a function of the time. TPEF images were collected at a range from 425-575 nm (fs pulses, 760 nm excitation conditions)

It should be understood that the appended drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to a fluorescent probe which can be selectively localized on the mitochondria of cells, a representative intracellular organelle. More particularly, the present invention relates to a two-photon fluorescent probe (SZn-Mito) which is a core material required for real-time imaging of zinc ion activity present inside the mitochondria via two-photon microscopy (TPM), a manufacturing process thereof, and an imaging method of free zinc ions within the mitochondria by using the same.

Hereinafter, the present invention will be described in more detail.

The present invention provides a two-photon fluorescent probe (SZn-Mito) selected from compounds represented by following Formulae 1 and 2.

[Formula 1]

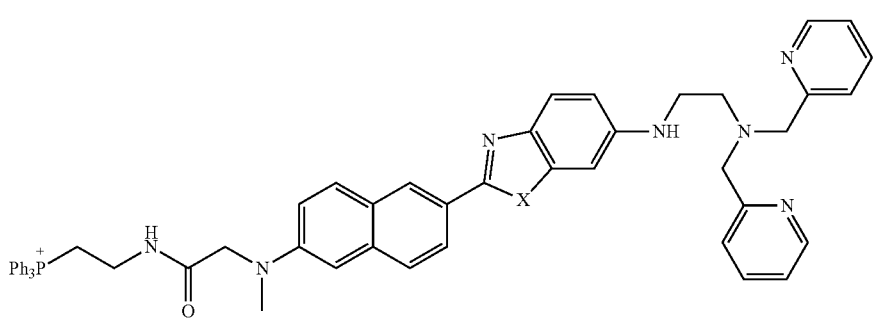

[Formula 2]

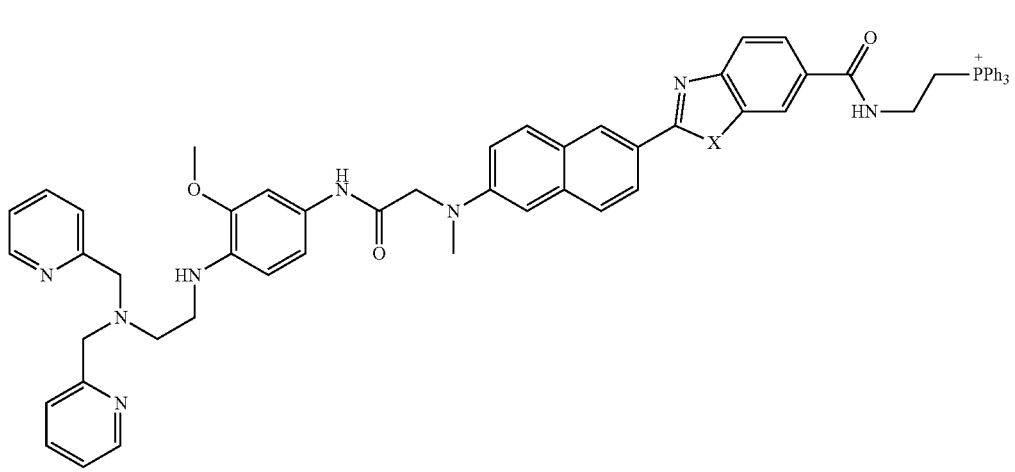

wherein X is S or O.

The two-photon fluorescent probe (SZn-Mito) of the present invention is characterized by incorporating triphenylphosphonium salt (TPP) as a mitochondrial probe and N,N-di-(2-picolyl)ethylenediamine (OPEN) as a zinc ion receptor into two-photon fluorescents 6-(benzo[d]thiazol-2-yl)-2-(N,N-dimethylamino)naphthalene (BTDAN) and 6-(benzo[d]oxazol-2-yl)-2-(N,N-dimethylamino)naphthalene (BODAN), respectively. Also, the triphenylphosphonium salt (TPP) and N,N-di-(2-picolyl)ethylenediamine (DPEN) in said compound are located as far away as possible from each other in order to minimize an interaction between them.

The two-photon fluorescent probe of the present invention can selectively stain the mitochondria of cells, an intracellular organelle, and react with zinc ions present therein, to thereby generate visible light fluorescence at a range from 400~650 nm. Therefore, it can be effectively used as a fluorescent probe suitable for visualizing selectivity on zinc ions and activity thereof.

Unlike the conventional one-photon fluorescent probes, the two-photon fluorescent probe of the present invention shows a deeper penetration depth in a range from 100~200 μm, and thus can detect zinc ions within the mitochondria of living cells and biological tissues at a depth of 100~200 μm. In addition, the two-photon fluorescent probe of the present invention is able to detect zinc ions continuously for 60 min or longer, more preferably for 30~90 min due to its optical stability inside the cells.

The present invention provides a method for manufacturing a two-photon fluorescent probe represented by above Formula 1 by reacting a compound represented by following Formula 3 with a compound represented by following Formula 4 under nitrogen atmosphere, followed by purification.

[Formula 3]

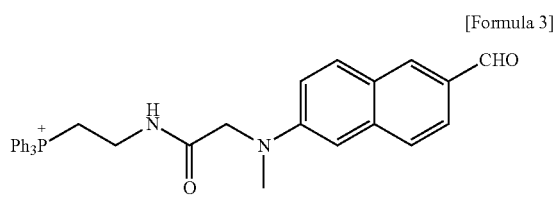

[Formula 4]

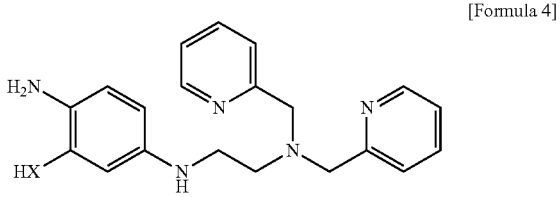

wherein X is S or O.

For example, the two-photon fluorescent probe represented by above Formula 1 can be manufactured by dropwise adding a compound represented by Formula 4 to a mixture of a compound represented by Formula 3 and chloroform in the presence of a catalytic amount of p-toluenesulfonic acid monohydrate, refluxing the resulting mixture, evaporating the solvent therefrom, and purifying it via column chromatography.

In addition, the present invention provides a method for manufacturing a two-photon fluorescent probe represented by above Formula 2 by reacting a compound represented by following Formula 5 with a compound represented by following Formula 6 under nitrogen atmosphere, followed by purification.

[Formula 5]

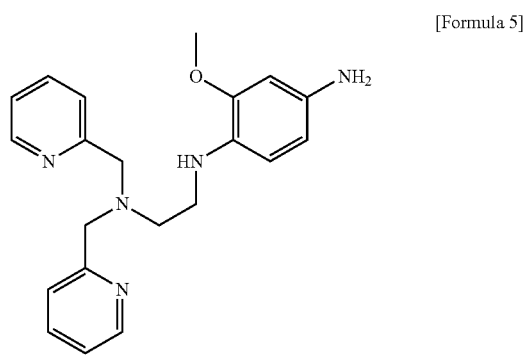

[Formula 6]

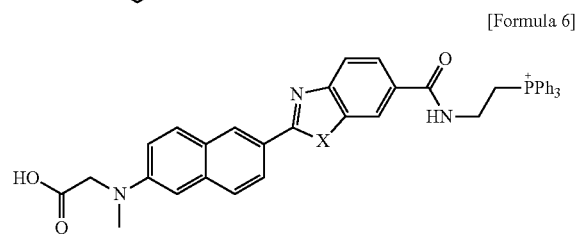

wherein X is S or O.

The two-photon fluorescent probe represented by Formula 2 can be manufactured by dropwise adding a compound represented by Formula 5 to a mixture of a compound represented by Formula 6 and dichloromethane in the presence of a catalytic amount of 1,3-dicyclohexyl carbodiimide, refluxing the resulting mixture, evaporating the solvent therefrom, and purifying it via column chromatography.

The present invention provides an imaging method of zinc ions present inside mitochondria, including:

(a) injecting the above two-photon fluorescent probe according into cells;

(b) reacting the two-photon fluorescent probe with zinc ions within the mitochondria of the cells, thereby generating fluorescence; and (c) observing the fluorescence with a two-photon microscope.

In step (a), the two-photon fluorescent probe can be injected into the cells at a very low concentration of $0.5 \times 10^{-6}$ M for 30 min, thereby being selectively localized on the mitochondria. After the injection, a near-infrared light corresponding to 760 nm can be used as an excitation source of the two-photon microscope, and its fluorescent range can be in 400~650 nm. When the two-photon fluorescent probe reacts with zinc, its fluorescence intensity is increased by 7-fold in the same fluorescence range, which allows to obtain two-photon microscopic images with high-resolution.

The two-photon microscope (TPM), which employs two near-infrared photons having low excitation energy as an excitation source, has a deeper penetration depth and localized excitation as compared with the one-photon microscope, and thus it has the advantage of being a long time imaging. The present invention is capable of effectively visualizing distribution and activity of zinc ions within the mitochondria of living cells or biological tissues.

Because two probes are introduced into one molecule, the two-photon fluorescent probe of the present invention can selectively stain the mitochondria, simultaneously with reacting with zinc ions, thereby generating strong fluorescence. In addition, the two-photon fluorescent probe of the present invention can be easily loaded onto the cells due to its water solubility and low molecular weight. Also, it can detect zinc ions present inside the mitochondria of living cells and biological tissues at a depth of 100~200 µm for a long time of 60 min or longer, and thus is capable of visualizing distribution and activity of zinc ions within the mitochondria of living cells or intact biological tissues.

EXAMPLES

The following examples illustrate the invention and are not intended to limit the same.

Example 1

Synthesis of a Two-Photon Fluorescent Probe (SZn-Mito)

(Synthesis of a Compound Represented by Formula 1)
Synthesis of Zn-Mito

6-Formyl-N-methyl-2-naphthylamine, (2-aminoethyl)triphenylphosphonium bromide and 6-aminobenzothiazole were synthesized according to conventional methods known in the art, respectively (*J. Am. Chem. Soc.* 2008, 130, 4246-4247; *J. Am. Chem. Soc.* 1985, 107, 217-226; and *Bioorg. Med. Chem.* 2009, 17, 7002-7007). Other compounds were synthesized according to following Scheme 1.

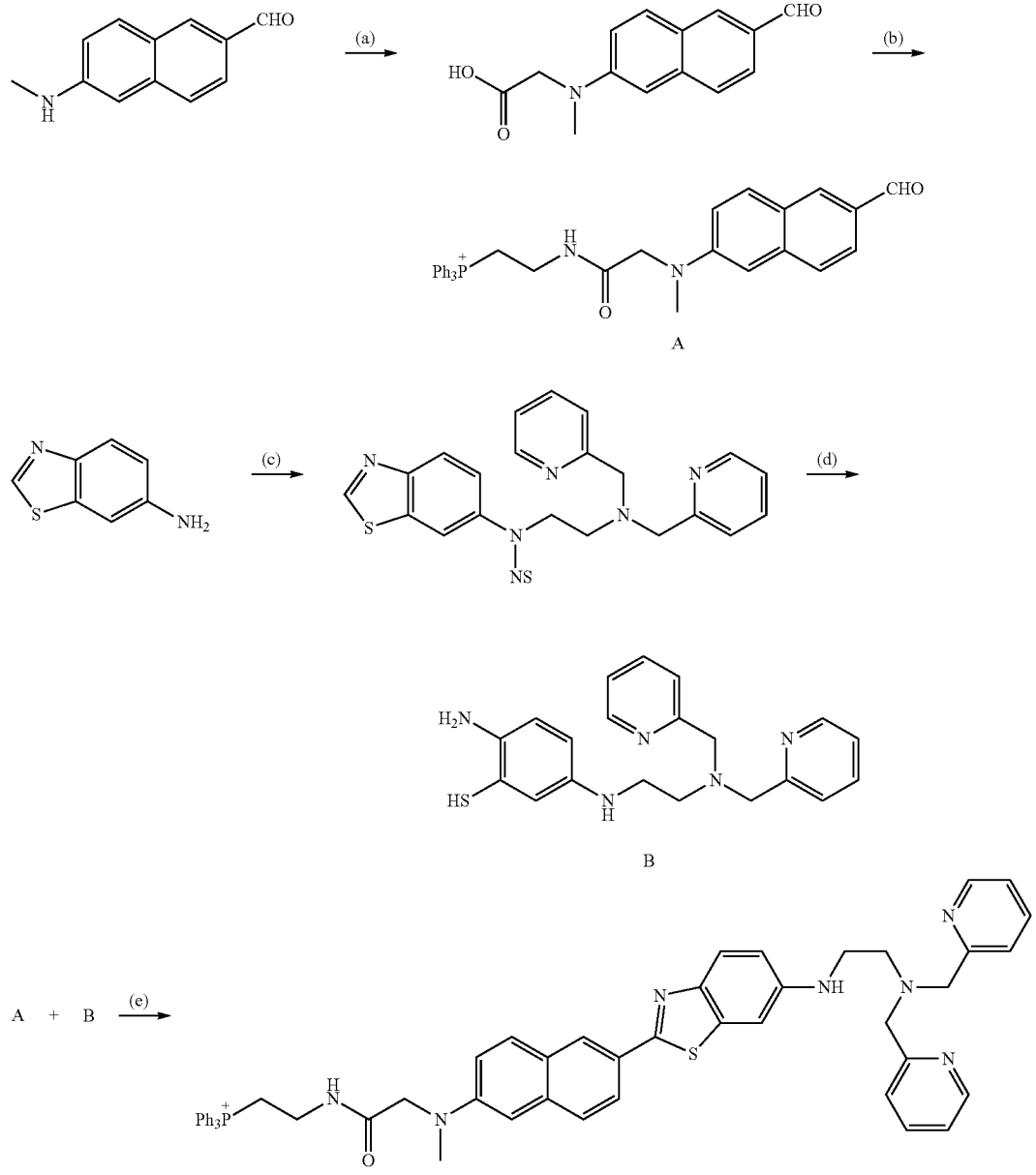

[Scheme 1]

SZn-Mito (a) is methyl bromoacetate, proton-sponge, CH₃CN; LiOH, THF-water;

(b) (2-aminoethyl)phosphonium bromide, DCC, HOBt;

(c) 4-nitrobenzenesulfonyl chloride, pyridine, DCM; 1,2-dibromoethane, Cs₂CO₃, DMF; 2,2'-dipicolylamine, K₂CO₃, KI, CH₃CN;

(d) thiophenol, K₂CO₃, DMF; ii: hydrazine, EtOH;

(e) p-toluenesulfonic acid, CHCl₃.

Hereinafter, the syntheses of the above compounds were described in more detail.

(1) Synthesis of Compound 1

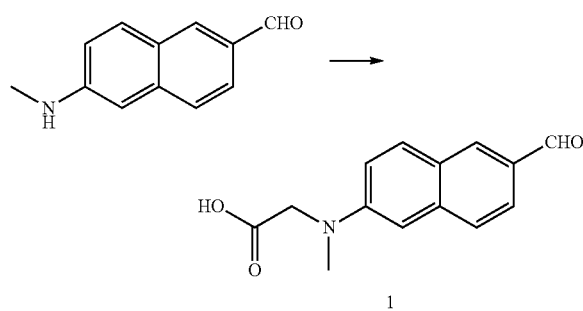

To a stirred solution of 6-formyl-N-methyl-2-naphthylamine (0.2 g, 1.1 mmol) and proton-sponge (0.44 g, 2.1 mmol) of dry CH₃CN (20 mL) was added methyl bromoacetate (0.30 mL, 3.3 mmol). The resulting mixture was stirred for 16 hr under nitrogen atmosphere with reflux so as to evaporate the solvent, and the thus generated product was dissolved in CH₂Cl₂ (50 mL). The CH₂Cl₂ layer in which the product was dissolved was successively washed with water and dilute sulfuric acid (H₂SO₄) several times, separated and dried over MgSO₄. After removing the solvent under reduced pressure, the crude product was purified via column chromatography with hexane/ethyl acetate (5:1) as an eluent to obtain a yellow solid (yield: 0.23 g (82%); m.p. 60☐).

¹H NMR (400 MHz, CDCl₃): d 9.99 (s, 1H), 8.17 (d, J=2.0 Hz, 1H), 7.81 (dd, J=8.8, 2.0 Hz, 1H), 7.80 (d, J=8.8 Hz, 1H), 7.65 (d, J=8.6 Hz, 1H), 7.08 (dd, J=8.6, 2.4 Hz, 1H), 6.87 (d, J=2.4 Hz, 1H), 4.21 (s, 2H), 3.73 (s, 3H), 3.19 (s, 3H).

¹³C NMR (100 MHz, CDCl₃): d191.9, 170.9, 149.3, 138.6, 134.7, 131.2, 131.1, 127.3, 125.8, 123.6, 115.9, 106.2, 54.4, 52.5, 40.1.

After that, the intermediate (0.20 g, 0.78 mmol) was dissolved in 3.0 mL of THF. To the resulting solution was added an aqueous solution (3.0 mL) of LiOH (0.20 g, 8.4 mmol), followed by stirring for 6 hr at room temperature. After evaporating the solvent from the mixture, water (4.0 mL) was added thereto. An water-soluble portion was acidified with 37% HCl at a temperature lower than 5☐ until pH reached 3. After the resulting precipitate was collected by filtration, it was washed with water, followed by washing with diethyl ether (yield: 0.17 g (90%); m.p. 182☐).

¹H NMR (400 MHz, CDCl₃): d 10.02 (s, 1H), 8.17 (d, J=2.0 Hz, 1H), 7.86 (d, J=8.8 Hz, 1H), 7.85 (dd, J=8.8, 2.0 Hz, 1H), 7.70 (d, J=8.8 Hz, 1H), 7.13 (dd, J=8.8, 2.4 Hz, 1H), 6.93 (d, J=2.4 Hz, 1H), 4.28 (s, 2H), 3.24 (s, 3H).

¹³H NMR (100 MHz, d₆-DMSO): d192.4, 172.1, 150.3, 138.7, 135.3, 131.3, 130.8, 127.3, 125.4, 123.4, 116.8, 105.8, 53.9, 40.9.

(2) Synthesis of Compound A

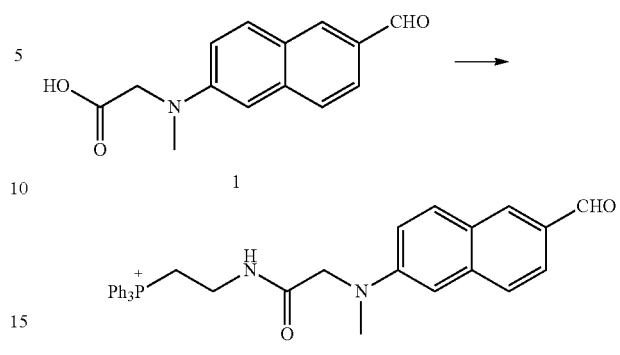

The compound 1 (0.10 g, 0.40 mmol), 1,3-dicyclohexyl carbodiimide (DCC, 0.094 g, 0.45 mmol) and 1-hydroxybenzotriazole (0.061 g, 0.45 mmol) were dissolved in CH₂Cl₂ (10 mL). The resulting mixture was stirred at room temperature for 1 hr under nitrogen atmosphere. To the stirred mixture was added (2-aminoethyl)triphenylphosphonium bromide (0.14 g, 0.37 mmol), followed by stirring for 16 hr. As a result, the solvent was evaporated, and the resulting product was dissolved in CH₃CN. Urea as a by-product was removed by filtration, and the resulting filtrate was concentrated under reduced pressure. The crude product was purified via column chromatography with CHCl₃/8% methanol as an eluent to obtain a compound A in the form of yellow bubbles (yield: 0.14 g (64%)).

¹H NMR (400 MHz, CDCl₃): d 9.97 (s, 1H), 9.07 (t, J=1.6 Hz, 1H, amide-NH), 8.10 (d, J=2.0 Hz, 1H), 7.82-7.72 (m, 11H), 7.70-7.64 (m, 7H), 7.15 (dd, J=8.8, 2.4 Hz, 1H), 6.91 (d, J=2.4 Hz, 1H), 4.17 (s, 2H), 3.86-3.79 (m, 2H), 3.73-3.67 (m, 2H), 3.29 (s, 3H).

¹³H NMR (100 MHz, CDCl₃): d191.9, 171.1, 149.7, 138.6, 135.4 (d, J=3.0 Hz), 134.9, 133.7 (d, J=9.9 Hz), 130.9, 130.8, 130.7 (d, J=12.9 Hz), 127.2, 125.7, 123.3, 117.3 (d, J=85.7 Hz), 116.6, 106.2, 56.9, 41.1, 33.7, 23.2 (d, J=48.6 Hz),

³¹P NMR (162 MHz, CDCl₃): d21.6 ppm.

(3) Synthesis of Compound 2

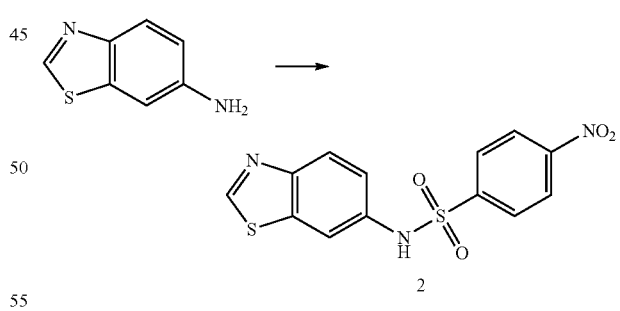

A solution of 6-aminobenzothiazole (1.6 g, 11 mmol) dissolved in 5 mL of CH₂Cl₂ was dropwisely added to a stirred solution of 4-nitrobenzenesulfonyl chloride (2.8 g, 13 mmol) and pyridine (1.7 mL, 21 mmol) dissolved in CH₂Cl₂ (30 mL). The resulting mixture was stirred at room temperature for 3 hr. After evaporating the solvent, the residue was dissolved in ethyl acetate, and extracted with water. The thus obtained organic layer was washed with a saturated water-soluble solution of NaHCO₃, separated, and dried over anhydrous magnesium sulfate (MgSO₄). After evaporating ethyl acetate, the resulting crude product was treated with CHCl₃ so as to generate a precipitate. The thus obtained precipitate was separated by filtration, washed with CHCl₃, and dried, to there by obtain a compound 2 as a brown solid (yield: 2.4 g (67%); m.p. 232□).

¹H NMR (400 MHz, d₆-DMSO): d10.87 (br s, 1H), 9.27 (s, 1H), 8.34 (d, J=6.8 Hz, 2H), 8.01 (d, J=6.8 Hz, 2H), 7.96 (d, J=8.8 Hz, 1H), 7.91 (d, J=2.0 Hz, 1H), 7.25 (dd, J=8.8, 2.0 Hz, 1H).

¹³H NMR (100 MHz, d₆-DMSO): d156.5, 150.8, 150.4, 145.2, 135.2, 135.0, 128.9, 125.3, 124.2, 120.9, 114.7.

(4) Synthesis of Compound 3

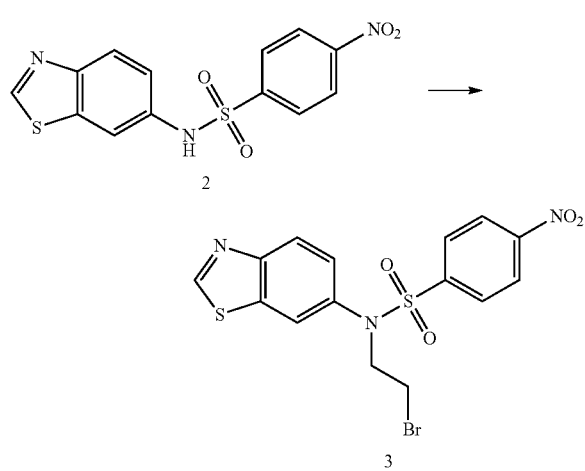

After the compound 2 (2.2 g, 6.6 mmol) dissolved in DMF (25 mL), 1,2-dibromoethane (5.7 mL, 66 mmol) and Cs₂CO₃ (2.6 g, 8.0 mmol) were mixed, the resulting mixture was stirred at 8□ for 16 hr. The mixture was diluted with 50 mL of CH₂Cl₂, and the diluted organic layer was washed with water, followed by washing with brine. As a result, the organic layer was separated, which was dried over anhydrous magnesium sulfate (MgSO₄) and evaporated. The resulting crude product was purified via column chromatography with hexane/ethyl acetate (4:1) as an eluent to obtain a compound 3 as a white solid (yield: 1.3 g (42%); m.p. 145□).

¹H NMR (400 MHz, CDCl₃): d9.11 (s, 1H), 8.32 (d, J=8.0 Hz, 2H), 8.08 (d, J=8.8 Hz, 1H), 7.88 (d, J=2.0 Hz, 1H), 7.81 (d, J=8.0 Hz, 2H), 7.08 (dd, J=8.8, 2.0 Hz, 1H), 4.04 (t, J=6.8 Hz, 2H), 3.43 (t, J=6.8 Hz, 2H).

¹³H NMR (100 MHz, CDCl₃): d156.4, 153.2, 150.4, 143.8, 135.2, 134.9, 129.0, 126.3, 124.6, 124.5, 123.8, 53.4, 28.9.

(5) Synthesis of Compound 4

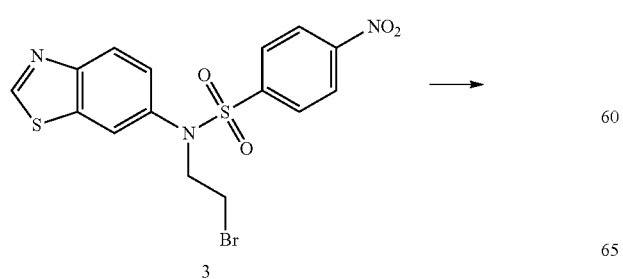

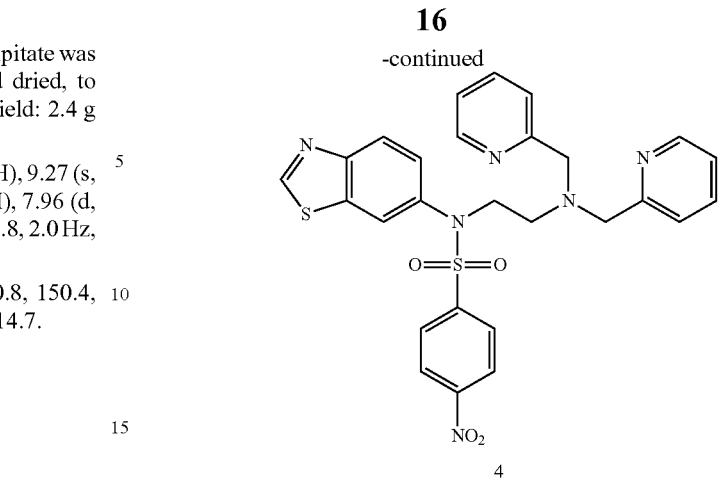

A mixture of the compound 3 (1.2 g, 2.7 mmol) dissolved in CH₃CN (40 mL), 2,2'-dipicolylamine (0.45 mL, 2.5 mmol), K₂CO₃ (0.94 g, 6.8 mmol) and KI (1.1 g, 6.7 mmol) was refluxed under nitrogen atmosphere for 3 hr. After evaporating the solvent, the residue was diluted with 2 N Na₂CO₃ (30 mL), and extracted with CH₂Cl₂. The thus separated organic layer was washed with brine, separated, dried over magnesium sulfate (MgSO₄), and evaporated. The resulting crude product was purified via column chromatography with CHCl₃/3% methanol as an eluent, and obtained a compound 4 in the form of light yellow bubbles (yield: 1.4 g (93%)).

¹H NMR (400 MHz, CDCl₃): d9.07 (s, 1H), 8:43-8.41 (m, 2H), 8.26 (d, J=8.8 Hz, 2H), 7.94 (d, J=8.8 Hz, 1H), 7.74 (d, J=8.8, 2H), 7.64 (d, J=2.4 Hz, 1H), 7.58 (td, J=8.0, 2.0 Hz, 2H), 7.40 (d, J=8.8 Hz, 2H), 7.11 (td, J=5.0, 1.2 Hz, 2H), 6.96 (dd, J=8.8, 2.4 Hz, 1H), 3.84 (t, J=6.2 Hz, 2H), 3.81 (s, 4H), 2.76 (t, J=6.2 Hz, 2H).

¹³C NMR (100 MHz, (CDCl₃): d158.7, 155.9, 152.6, 150.0, 148.9, 143.7, 136.5, 135.6, 134.4, 128.8, 126.0, 124.3, 123.9, 123.5, 123.1, 122.2, 60.5, 52.2, 49.9.

(6) Synthesis of Compound 5

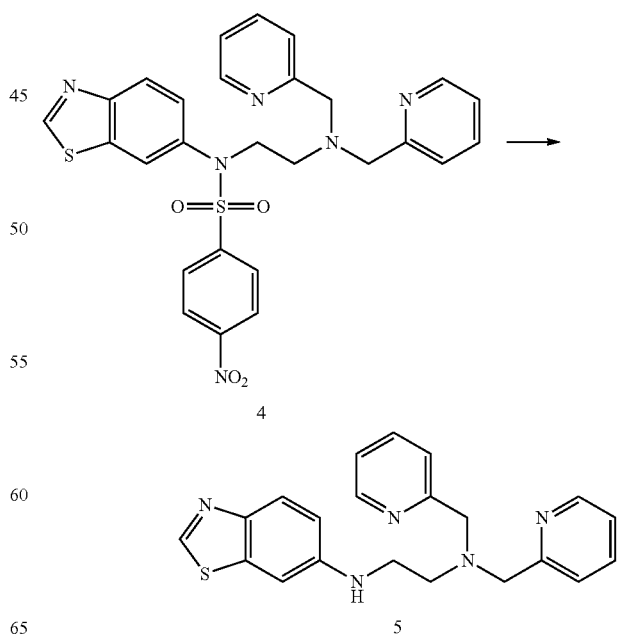

To a dispersion of the compound 4 (1.0 g, 1.8 mmol) dissolved in DMF (10 mL) and K₂CO₃ (0.74 g, 5.4 mmol) was added thiophenol (0.55 mL, 5.4 mmol), followed by stirring for 16 hr at room temperature. After diluting the resulting mixture with CH₂Cl₂ (40 mL), organic layers were combined and extracted with water. The combined organic layer was washed with brine, separated, dried over anhydrous magnesium sulfate (MgSO₄), and evaporated. The resulting crude product was purified via column chromatography with CHCl₃/5% methanol as an eluent to obtain a sticky compound 5 (yield: 0.55 g (82%)).

¹H NMR (400 MHz, CDCl₃): d8.61 (s, 1H), 8.56-8.54 (m, 2H), 7.84 (d, J=8.8 Hz, 1H), 7.59 (td, J=8.0, 2.0 Hz, 2H), 7.38 (d, J=8.0 Hz, 2H), 7.12 (td, J=5.2, 1.2 Hz, 2H), 6.94 (d, J=2.4 Hz, 1H), 6.82 (dd, J=8.8, 2.4 Hz, 1H), 5.22 (brs, 1H), 3.89 (5, 4H), 3.19 (t, J=6.0 Hz, 2H), 2.91 (t, J=6.0 Hz, 2H).

and heated to 80□ for 3 hr. After evaporating the resulting mixture, water (20 mL) was added thereto, and its pH was adjusted to 5 with HCl$_{(aq)}$. The thus obtained mixture was extracted with CH₂Cl₂ so as to separate an organic layer, which was dried over magnesium sulfate (MgSO₄) and evaporated and obtained a sticky compound B (yield: 0.25 g (52%)).

¹H NMR (400 MHz, CDCl₃): d8.53-8.51 (m, 2H), 7.60 (td, J=8.0, 2.0 Hz, 2H), 7.39 (d, J=7.6 Hz, 2H), 7.12 (td, J=5.2, 1.2 Hz, 2H), 6.63 (d, J=2.4 Hz, 1H), 6.58 (d, J=8.4 Hz, 1H), 6.42 (dd, J=8.4, 2.4 Hz, 1H), 3.85 (s, 4H), 3.72 (brs, 1H), 3.08 (t, J=6.0 Hz, 2H), 2.91 (t, J=6.0 Hz, 2H).

¹³C NMR (100 MHz, CDCl₃): d159.2, 149.2, 142.0, 137.9, 136.5, 123.2, 122.2, 118.6, 117.2, 114.9, 114.4, 60.6, 53.2, 42.8.

(8) Synthesis of SZn-Mito

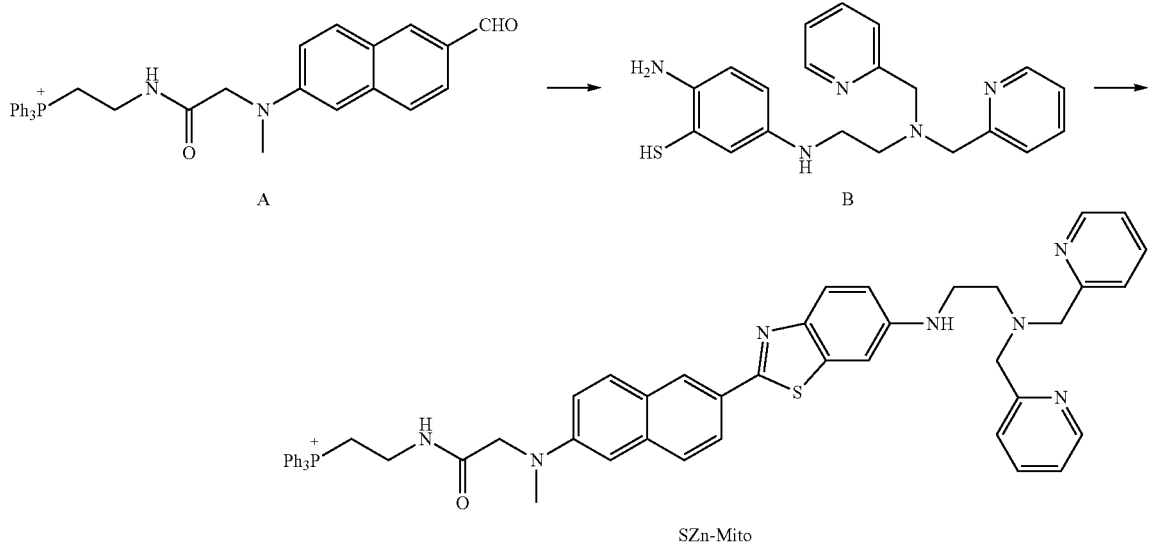

¹³C NMR (100 MHz, CDCl₃): d159.1, 149.2, 148.6, 147.3, 145.7, 136.6, 135.9, 123.7, 123.3, 122.3, 115.1, 101.9, 60.6, 52.8, 42.0.

(7) Synthesis of Compound B

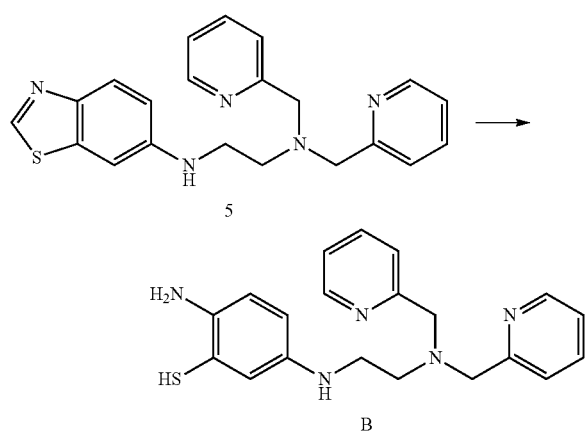

The compound 5 (0.50 g, 1.3 mmol) and hydrazine monohydrate (1.0 mL, 21 mmol) were added to ethanol (20 mL)

Under nitrogen atmosphere, a solution in which the compound B (0.070 g, 0.19 mmol) was added to CHCl₃ (5.0 mL) was dropwisely added to a stirred solution in which the compound A (0.11 g, 0.18 mmol) and p-toluenesulfonic acid monohydrate (0.012 g, 0.063 mmol) were added to CHCl₃ (15 mL). The resulting mixture was then refluxed for 16 hr. After evaporating the solvent, the resulting crude product was purified via column chromatography with CHCl₃/10% methanol as an eluent to obtain a two-photon fluorescent probe (SZn-Mito) in the form of yellow bubbles (yield: 0.070 g (40%), mp: 64□).

¹H NMR (400 MHz, CDCl₃): d8.97 (t. J=5.6 Hz, 1H, amide-NH), 8.56-8.54 (m, 2H), 8.24 (d, J=2.0 Hz, 1H), 7.95 (dd, J=8.8, 2.0 Hz, 1H), 7.77-7.72 (m, 9H), 7.70-7.59 (m, 11H), 7.42 (d, J=8.0 Hz, 2H), 7.15-7.10 (m, 3H), 6.92-6.90 (m, 2H), 6.79 (dd, J=7.6, 2.0 Hz, 1H), 4.77 (brs, 1H), 4.06 (s, 2H), 3.95 (s, 4H), 3.85-3.78 (m, 2H), 3.72-3.67 (m, 2H), 3.26 (s, 3H), 3.23 (t, J=5.6 Hz, 2H), 2.95 (t, J=5.6 Hz, 2H).

¹³H NMR (100 MHz, CDCl₃): d171.4, 163.5, 158.7, 149.1, 148.1, 146.7, 146.6, 136.9, 136.7, 135.9, 135.4 (d, J=3 Hz), 133.7 (d, J=10.6 Hz), 130.7 (d, J=12.9 Hz), 129.8, 127.7, 127.0, 126.6, 126.4, 124.6, 123.5, 123.1, 122.4, 117.3 (d, J=85.7 Hz), 116.8, 114.7, 106.5, 102.3, 60.5, 57.1, 52.8, 41.9, 41.1, 33.7, 23.2 (d, J=48.6 Hz).

$^{31}$P NMR (162 MHz, CDCl$_3$): d21.7 ppm; HRMS (FAB$^+$): m/z calcd for [C$_{54}$H$_{51}$N$_7$OPS]$^+$: 876.3613. found: 876.3617.

Example 2

Synthesis of a Two-Photon Fluorescent Probe (SZn-Mito)

(Synthesis of a Compound Represented by Formula 2)

Example 3

Optical and Physical Properties of a Two-Photon Fluorescent Probe

In order to investigate optical and physical properties of the two-photon fluorescent probe (SZn-Mito), the following experiment was carried out by using a MOPS (3-(N-morpholino)propane sulfonic acid) buffer.

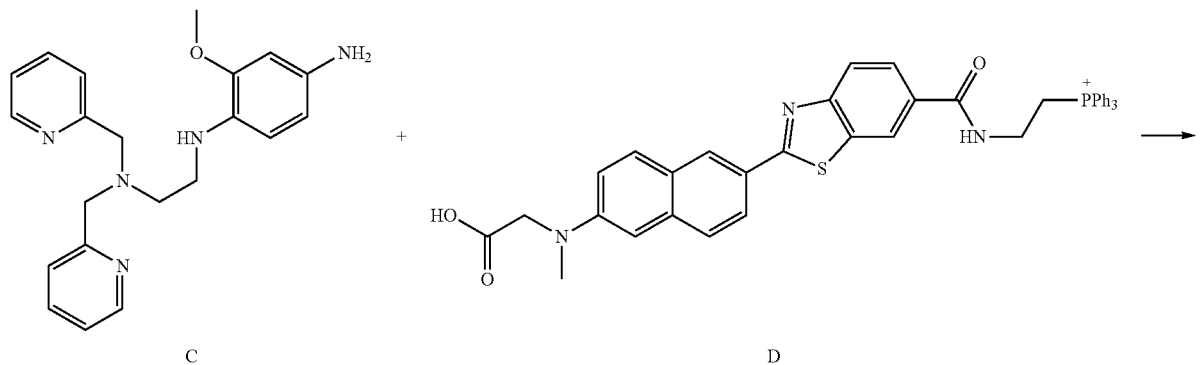

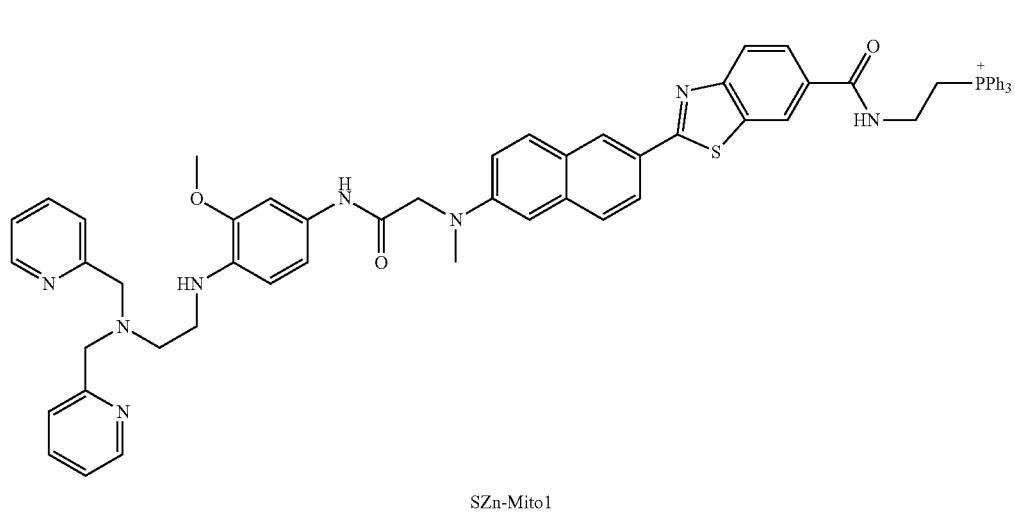

SZn-Mito1

Under nitrogen atmosphere, a solution in which the compound C (0.150 g, 0.41 mmol), compound D (0.37 g, 0.50 mmol) and DCC (0.11 g, 0.53 mmol) were added to CH$_2$Cl$_2$ (5.0 mL) was stirred for 10 hr. After evaporating the solvent the resulting crude product was purified via column chromatography with CHCl$_3$/10% methanol as an eluent to obtain a two-photon fluorescent probe (SZn-Mito1) (yield: 0.18 g (40%)).

$^1$H NMR (400 MHz, CDCl$_3$): δ9.59 (s, 1H), 8.65 (s, 1H), 8.50 (m, 3H), 8.12 (m, 4H), 8.05 (d, 1H, J=9 Hz), 7.84 (m, 7H), 7.76 (m, 4H), 7.68 (m, 6H), 7.62 (td, 2H, J=8 Hz, J=2 Hz), 7.50 (d, 2H, J=8 Hz), 7.12 (m, 2H), 6.71 (dd, 1H, J=8, J=2 Hz), 6.38 (d, 1H, J=8 Hz), 4.11 (s, 2H), 4.02 (m, 4H), 3.89 (s, 4H), 3.85 (s, 3H), 3.24 (S, 3H), 3.16 (t, 2H, J=6 Hz), 2.86 (t, 2H, J=6 Hz).

Figure 2:
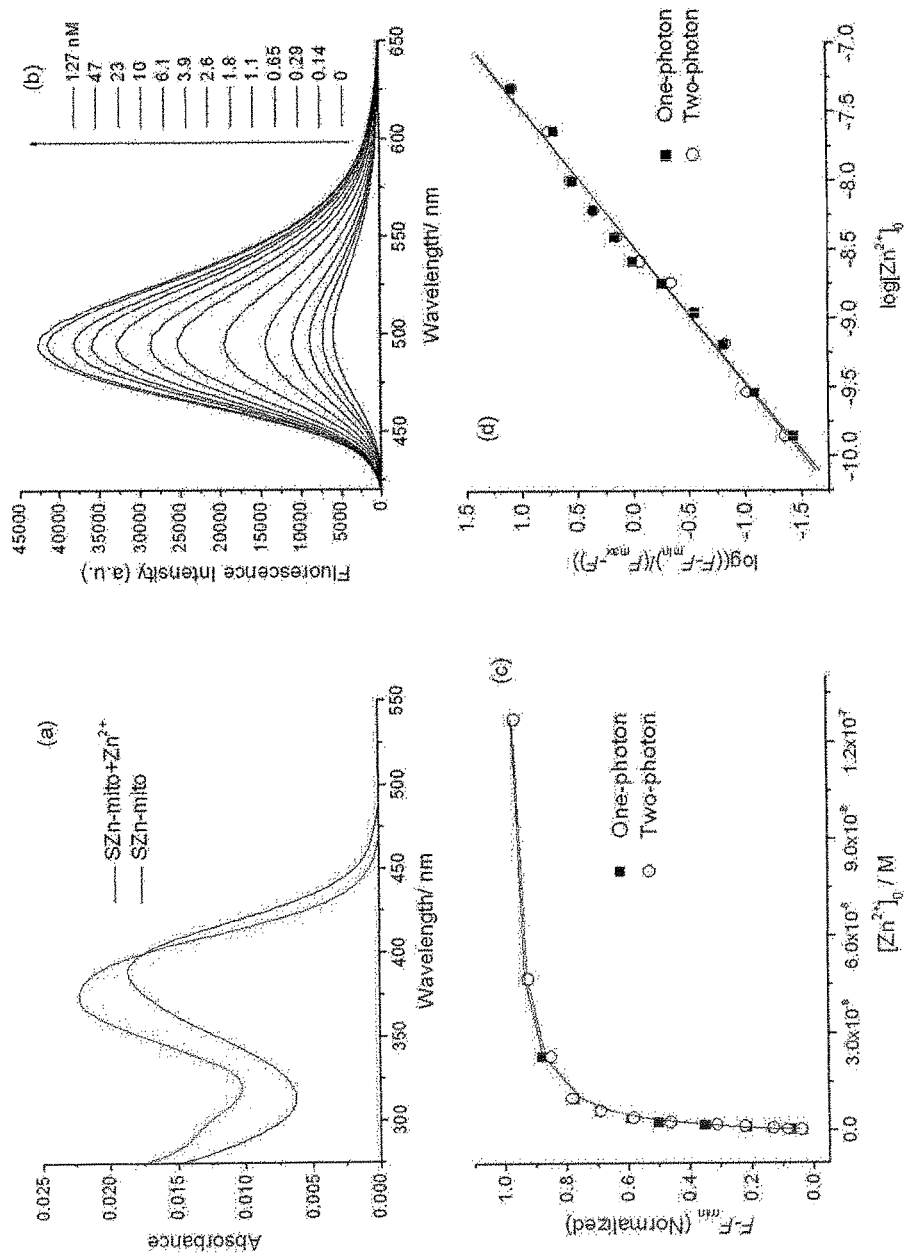
FIG. 2 shows graphs showing (a) one-photon absorption, (b) emission spectra (30 mM MOPS, 100 mM KCl, 10 mM EGTA, pH 7.2) of SZn-Mito in the presence of free $Zn^{2+}$ (0-127 nM), (c) one-photon (■) and two-photon (□) fluorescence titration curves for the complexation of SZn-Mito and free $Zn^{2+}$ (0-127 nM), and (d) a Hill plot for the complexation of SZn-Mito and free $Zn^{2+}$ (0-127 nM). Here, excitation wavelengths for one- and two-photon processes are 385 and 760 nm, respectively.
Figure 3:
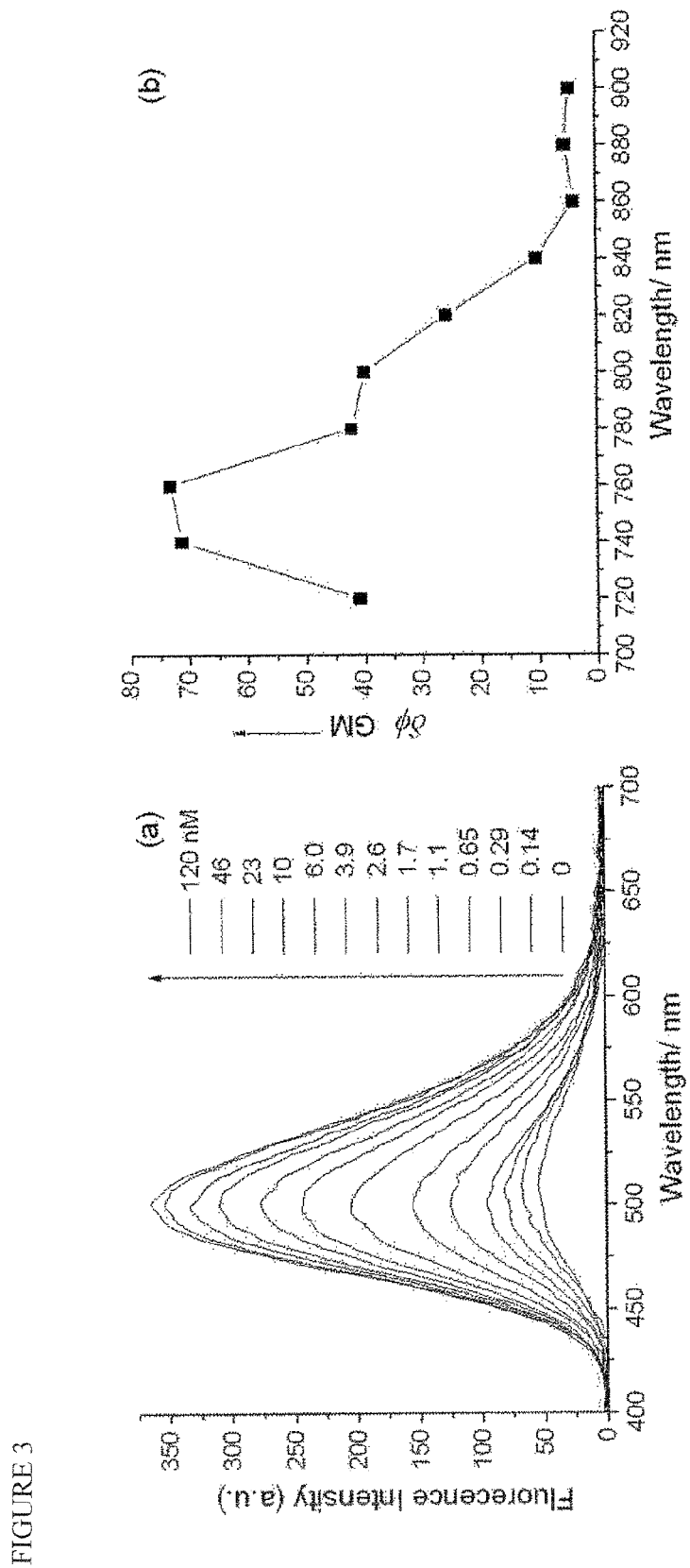
FIG. 3 shows graphs showing (a) two-photon fluorescence spectra of 1 SZn-Mito in the presence of free $Zn^{2+}$ (0-120 nM) in which an excitation wavelength was 760 nm, (b) a two-photon action spectrum of SZn-Mito in the presence of 47 nM free $Zn^{2+}$.

When a small amount of zinc ions (Zn$^{2+}$) were added to the two-photon fluorescent probe (SZn-Mito) in the MOPS buffer, fluorescent intensity was gradually increased as a function of the concentration of metal ions (there was no effect on the absorption spectrum) (see FIG. 2). It was predicted as a result of blocking the photo-induced electron transfer (PeT) process caused by complexation with metal ions. It was found that almost the same results were observed in the TP process (see FIG. 3(a)).

As a result of measuring a fluorescence increase factor (FEF=(F−F$_{min}$)/F$_{min}$) value of the two-photon fluorescent probe (SZn-Mito) by one- and two-photon processes, the FEF value was represented as 7 in the presence of excessive zinc ions (Table 1).

TABLE 1

Optical and physical data of two-photon fluorescent probe

| Compd[a] | $\lambda_{max}^{(1)}$ ($10^{-4}$ ε)[b] | $\lambda_{max}^{fl}$ [c] | F[d] | $K_d^{OP}/K_d^{TP}$ [e] | FEF[f] | $\lambda_{max}^{(2)}$ [g] | d[h] | Fd[i] |
|---|---|---|---|---|---|---|---|---|
| SZn-Mito | 388 (1.87) | 500 | 0.15 | — | — | | | |
| SZn-Mito + Zn$^{2+}$ | 375 (2.31) | 493 | 0.92 | 3.1/3.1 | 7(7) | 760 | 96 | 75 |

[a]All data was measured in the absence or presence of zinc ions (Zn$^{2+}$), and MOPS was used as a buffer (30 mM MOPS, 100 mM KCl, 10 mM EGTA, pH 7.2).
[b]A unit of one-photon absorption spectra $l_{max}$ was nm. The number in parenthesis was a molar excitation coefficient and its unit was M$^{-1}$cm$^{-1}$.
[c]A unit of one-photon emission spectra $l_{max}$ was nm.
[d]Fluorescence quantum yield, ±15%.
[e]A dissociation constant of zinc ions measured by one-photon ($K_d^{OP}$) and two-photon ($K_d^{TP}$) processes (nM unit), ±10%.
[f]Fluorescence enhancement factor (FF$_{min}$)/F$_{min}$ measured by a one-photon process. The number in parenthesis was the value measured by a two-photon process.
[g]$l_{max}$ values of two-photon excitation spectra. The unit was nm.
[h]two-photon absorption efficiency. The unit was GM. ± 15%.
[i]two-photon fluorescence efficiency. The unit was GM. ± 15%.

Example 4

Mitochondrial Selectivity of Two-Photon Fluorescent Probe

Figure 5:
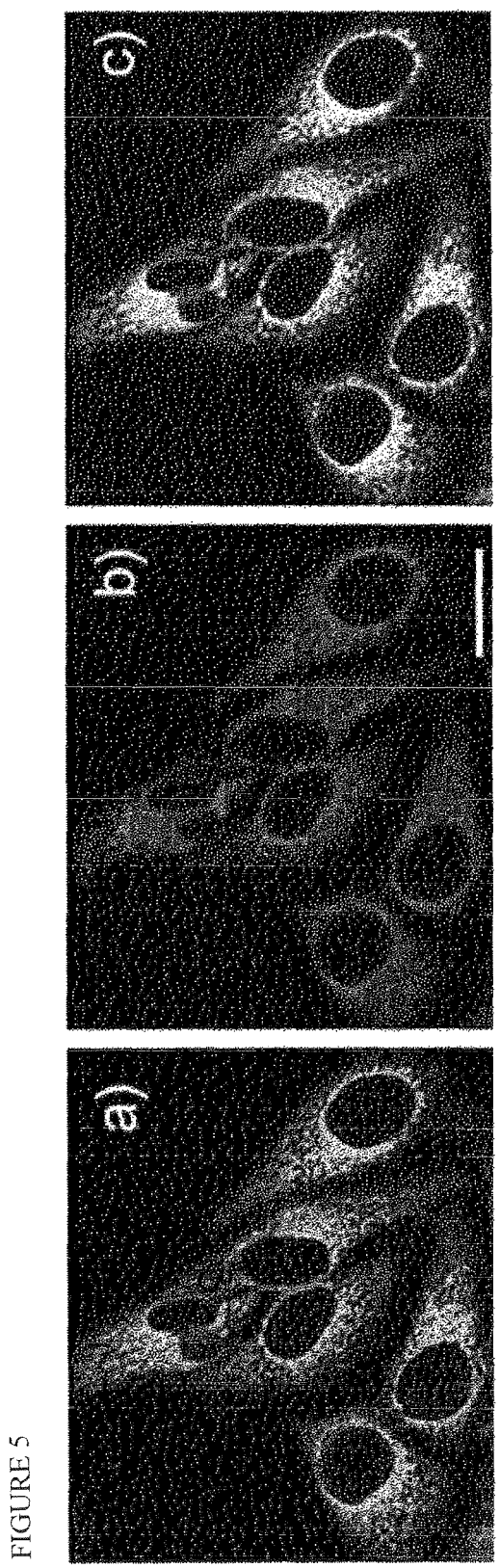
FIG. 5 shows (a) a bright field image, (b) a TPM image of HeLa cells labeled with SZn-Mito (5) and MitoTracker 5 at 37° C. for 30 min, (c) an OPM image thereof, and (d) a colocalized image thereof. Excitation wavelengths of one-photon and two-photon processes were 514 and 760 nm, respectively, and their emission was collected at 500-650 and 425-575 nm, respectively. A scale bar was 20. The cells indicated therein were representative images obtained by repetitive experiments.

In order to examine selectivity of the two-photon fluorescent probe according to the present invention specific to the mitochondria, the following experiment was carried out. For confirming whether the strong green fluorescence image of the two-photon fluorescent probe as shown in FIG. 5a can actually visualize the mitochondria, HeLa cells were stained with MitoTracker Red (Invitrogen) previously known as a conventional one-photon microscopic probe, a one-photon red fluorescence image thereof was obtained (FIG. 5b), and then, two images were overlapped (FIGS. 5a and 5b). The thus overlapped image is shown in FIG. 5c. Referring to FIG. 5c, two images obtained after staining with two dyes, respectively (FIGS. 5a and 5b), were identical to each other. These results suggest that it is possible to obtain accurate imaging of the mitochondria by using the two-photon fluorescent probe of the present invention.

Example 5

Zinc Ion Dissociation Constant and Selectivity of a Two-Photon Fluorescent Probe In order to confirm that the two-photon fluorescent probe of the present invention has a dissociation constant of zinc ions and selectivity therefor suitable for the detection of intracellular zinc ions, the following experiment was conducted.

MOPS (4-morpholinepropanesulfonic acid) buffers (30 mM, pH 7.2, 0.1 M KCl) including varying amounts of ZnSO$_4$ and 10 mM EGTA (ethylene glycol-bis(2-aminoethylether)-N,N,N',N'-tetraacetic acid) were prepared.

The concentration of free Zn$^{2+}$ ([Zn$^{2+}$]$_{free}$) was calculated from $K_{Zn\text{-}EGTA}^{app}$, [EGTA] total, and [Zn$^{2+}$]$_{total}$ by using following Equation 1:

$$[Zn^{2+}]_{free} = [Zn^{2+}]_{total} / (\alpha_{Zn} \times K_{Zn\text{-}EGTA}^{app} \times [EGTA]_{free}) \quad [\text{Equation 1}]$$

wherein, $$K_{Zn\text{-}EGTA} = K_{Zn\text{-}EGTA} / \alpha_{Zn}\alpha_{EGTA},$$

$$\alpha_{Zn} = 1 + 10^{(pH-pK_1)} + 10^{(2pH-pK_1-pK_2)} + 10^{(3pH-pK_1-pK_2-pK_3)} \ldots,$$

$$\alpha_{EGTA} = 1 + 10^{(pK_1-pH+0.11)} + 10^{(pK_1+pK_2-2pH+0.22)} + 10^{(pK_1+pK_2+pK_3-3pH+0.33)} \ldots,$$

$$[EGTA]_{free} = [EGTA]_{total} - [Zn^{2+}]_{total}\text{이}$$

thus, $$K_{Zn\text{-}EGTA}^{app} = \frac{K_{Zn\text{-}EGTA}(1 + 10^{(pK_{Zn\text{-}EGTA}-pH)})}{(1 + 10^{(pH-pK_{Zn})})\left(\begin{array}{c}1 + 10^{(pK_1-pH)} + \\ 10^{(pK_1+pK_2-2pH)}\end{array}\right)}$$

After that, the stability constant of a Zn$^{2+}$ complex of EGTA (K$_{Zn\text{-}EGTA}$) was obtained by a conventional method known in the art. As a result, for EGTA (pH 7.2, 0.1 M KCl, 25□), pK$_1$=9.40, pK$_2$=8.79, pK$_3$=2.70, and log K$_{Zn\text{-}EGTA}$=12.6 were obtained.

All protonation constants at 0.1 M ion strength workout were corrected upward by 0.11, [EGTA]total was fixed at 10 mM, and [Zn$^{2+}$]total was in the range from 0 to 9.5 mM.

The concentration of [Zn$^{2+}$]$_{free}$ calculated for each solution is shown in following Table 2.

TABLE 2

| [Zn$^{2+}$]$_{total}$ (mM) | 0.50 | 1.00 | 1.50 | 2.00 | 2.50 | 3.00 | 3.50 | 4.00 | 4.99 | 5.99 | 6.98 | 7.98 | 8.97 | 9.47 |
|---|---|---|---|---|---|---|---|---|---|---|---|---|---|---|
| [Zn$^{2+}$]$_{free}$ (mM) | 0.14 | 0.29 | 0.46 | 0.66 | 0.87 | 1.1 | 1.4 | 1.8 | 2.6 | 3.9 | 6.1 | 10 | 22 | 47 |

In order to clearly determine a dissociation constant of the two-photon fluorescent probe, FIG. 2c as a fluorescence titration curve was obtained from FIG. 2b by using following Equation 2.

$$F = F_0 + (F_{max} - F_0) \frac{[Zn^{2-}]_{free}}{K_d - [Zn^{2+}]_{free}}$$ [Equation 2]

wherein F is a fluorescence intensity. $F_{max}$ is a maximum fluorescence intensity, $F_o$ is a fluorescence intensity in the absence of $Zn^{2+}$, and $[Zn^{2+}]_{free}$ is a concentration of free $Zn^{2+}$.

$K_d$ values that well complies with the titration curve (FIG. 2c) according to Equation 2 were calculated by using a commercial Origin software. Also, in order to determine $K_d$ values in the two-photon process, two-photon fluorescence that was excited by a mode-locked titanium-sapphire laser light source (Coherent Chameleon, 90 MHz, 200 fs) which was set to a wavelength of 760 nm and an output of 1180 mW, was collected with a CDC camera, to thereby obtain a two-photon excitation fluorescence spectrum. A two-photon excitation fluorescence titration curve was obtained, which was fitted to Equation 2 (FIGS. 2c and 2d).

Referring to FIG. 2c, the dissociation constants of SZn-Mito calculated from the one-photon and two-photon fluorescence titration curves were 3.1 nM, respectively (see Table 1). Here, the detection limit of the two-photon fluorescent probe was an nM range area.

Figure 4:
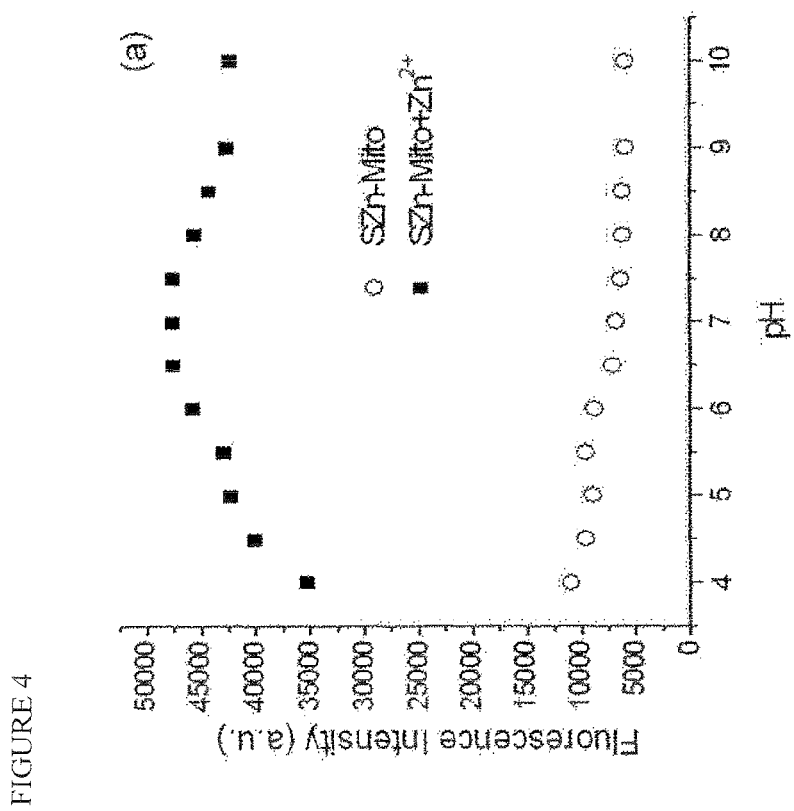
FIG. 4 shows a graph illustrating (a) the effect of pH on fluorescence intensity of 1 SZn-Mito one-photon in the absence (○) and presence (■) of 1.0 free $Zn^{2+}$ in a MOPS buffer (30 mM MOPS, 100 mM KCl, pH 7.2) in which an excitation wavelength was 380 nM, and (b) relative fluorescence intensities of 1.0 μM SZn-Mito in a MOPS buffer in the presence of 1.0 mM $Na^+$, $K^+$, $Ca^{2+}$, $Mg^{2+}$; 1.0 μM $Mn^{2+}$, $Fe^{2+}$, $Co^{2+}$, $Ni^{2+}$, $Cu^{2+}$, and $Cd^{2+}$ (empty bar) and after the addition of 1.0 μM $Zn^{2+}$ thereto (filled bar)

The selectivity for metal cations was determined by using the MOPS buffer (30 mM MOPS, 100 mM KCl, 10 mM EGTA, pH 7.2) including the two-photon fluorescent probe. As can be seen from FIG. 4, the two-photon fluorescent probe shoed higher selectivity for $Zn^{2+}$ as compared with $Na^+$, $K^+$, $Ca^{2+}$, $Mg^{2+}$, $Mn^{2+}$, $Fe^{2+}$, and $Fe^{3+}$, and exhibited relatively high selectivity for $Cd^{2+}$ ((b) of FIG. 4). In the presence of $Co^{2+}$, $Ni^{2+}$ and $Cu^{2+}$, fluorescence was decreased due to a metal-to-ligand electron transfer caused by excitation. However, because there are very little metal ions such as $Co^{2+}$, $Ni^{2+}$ and $Cu^{2+}$ inside the cells, the two-photon fluorescent probe of the present invention has an advantage that it can detect zinc ions ($Zn^{2+}$) without the interference caused by competition with other metal ions. Also, the two-photon fluorescent probe (SZn-Mito) of the present invention has a characteristic of being unreacted at physiological pH ((a) of FIG. 4).

Example 6

Activity Imaging of Zinc Ions within the Mitochondria by Using a Two-Photon Fluorescent Probe and a Two-Photon Microscope In order to confirm whether the two-photon fluorescent probe of the present invention can detect intracellular zinc ions, the effect of the two-photon fluorescent probe (SZn-Mito) on the cells was examined by the following toxicity test. As a result of measuring the toxicity by using a CCK-8 kit, it was found that the two-photon fluorescent probe showed negligible and extremely low toxicity. Also, the TFEP intensity of HeLa cells labeled with SZn-Mito at a certain area was not decreased at all even when exposure to continuous fs-pulse radiation for 60 min, which suggests that it has a high light stability.

Then, whether the two-photon fluorescent probe of the present invention can monitor the change in zinc ions in living cells was tested as follows.

When DTDP (2,2'-dithiodipyridine; 150 mM), reagent capable of inducing dissociation of $Zn^{2+}$ ions from $Zn^{2+}$-binding proteins, was added to the HeLa cells labeled with the two-photon fluorescent probe (SZn-Mito), the TPEF intensity was increased. When CCCP (carbonyl cyanide m-chlorophenylhydrazone; 10 mM), a compound capable of disrupting a transmembrane potential difference of the mitochondria and increasing the release of cations within the mitochondria, was added thereto, the TPEF intensity was decreased. Also, when the HeLa cells were treated with 100 mM $Zn^{2+}$ and 100 mM pyrithione (2-mercaptopyridine N-oxide), a reagent capable of delivering $Zn^{2+}$ to the cytoplasm, the TPEF intensity was increased, and when they were treated with CCCP, the TPEF intensity was decreased (FIG. 1).

These results confirmed that the two-photon fluorescent probe (SZn-Mito) of the present invention can detect intracellular zinc ions ($Zn^{2+}$) of living cells for a long time in the presence of minimum interference from competition with other metal ions, pH, cytotoxicity and light stability.

Example 7

Internal Imaging of Rat Hippocampal Slices by Using a Two-Photon Fluorescent Probe and a Two-Photon Microscope In order to demonstrate the utility of the two-photon fluorescent probe according to the present invention for imaging of cells within living tissues, fine slices of mouse hippocampal projections were monitored as follows. In this experiment, the fine slices of mouse hippocampal projections were incubated with 10 μM of the two-photon fluorescent probe (SZn-Mito) for 30 min at 37□, followed by obtaining a two-photon microscopic image. Because the slice from a 14-day-old mice were too large to be shown only in one image, a plurality of TPM images were obtained from the same plane at a thickness of about 100-200 μm depth and combined.

Figure 6:
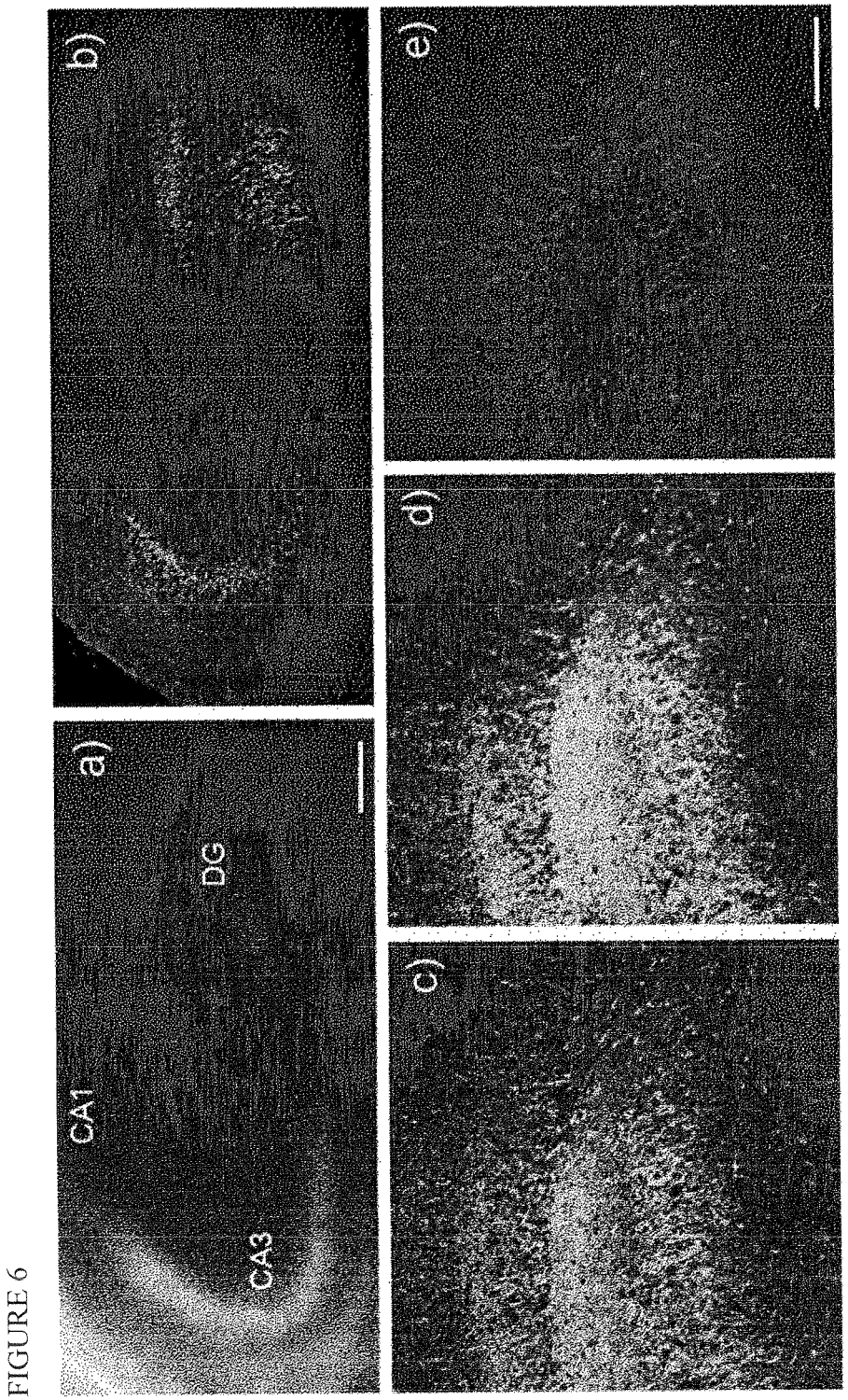
FIG. 6 shows images of rat hippocampal slices stained with 10 SZn-Mito for 30 min, in which (a) represents a bright field image of the dentate gyrus (DG) and CA1-CA3 areas (10× magnification), (b) represents a 25 TPM combined image at a depth of about 100-200 μm in accordance with the direction of the z-axis, (c) and (d) represent images of the DG area (red box of (b)) at a depth of about ~100 μm before and after the addition of 150 DTDP to an imaging solution (40× magnification), and (e) represents an image after the addition of 10 CCCP to (d) (scale bar: 300 (a) and 75 (e) mm).

FIG. 6 represents the image according to this experiment. In particular, (a) represents a bright field image of the dentate gyrus (DG) and CA1-CA3 areas (10× magnification), (b) represents a 25 TPM combined image at a depth of about 100-200 μm in accordance with the direction of the z-axis, (c) and (d) represent images of the DG area (red box of (b)) at a depth of about ~100 μm before and after the addition of 150 DTDP to an imaging solution (40× magnification), and (e) represents an image after the addition of 10 CCCP to (d).

Referring to FIG. 6(a), the strong fluorescence intensity was detected at the stratum lucidum of the CA3 area and the hilus of the dentate gyrus. The images obtained from higher magnification clearly showed that $[Zn^{2+}]_m$ was concentrated at the mossy fiber axon of pyramidal neurons of the CA3 area (see FIG. 6(b)). Also, when the slice was treated with DRDP capable of inducing an increase in $[Zn^{2+}]_m$, the two-photon fluorescence was increased radically. When the slice was treated with CCCP capable of inhibiting the activity of cations within the mitochondria, TPEF was decreased. These results clearly demonstrated the above observation (see FIGS. 6(d) and (e)).

In addition, the TPM (two-photon microscope) images obtained at a depth of 100-200 μm clearly showed the distribution of $[Zn^{2+}]_m$ present in the mossy fibers of the dentate gyrus neurons located near the hilum according to the z-axis depth (that is, thickness).

These results described above have confirmed that the two-photon fluorescent probe (SZn-Mito) of the present invention can effectively detect free $Zn^{2+}$ present inside biological tissues, especially the mitochondria at a depth of 100 to 200 μm by using TPM.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A two-photon fluorescent probe selected from the compounds represented by following Formulae 1 and 2:

[Formula 1]

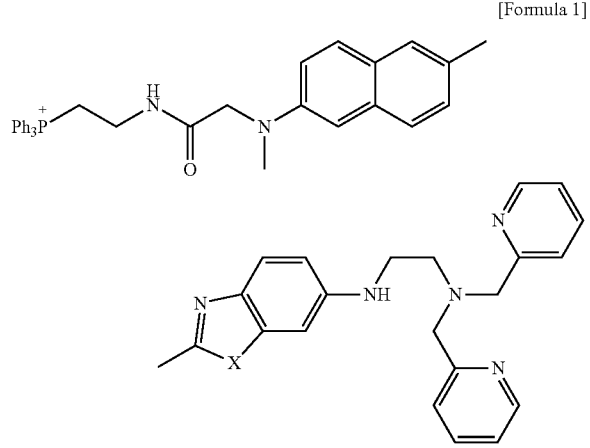

[Formula 2]

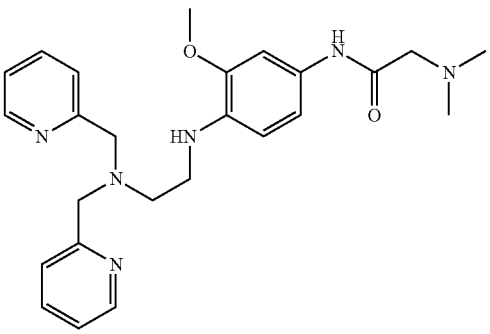

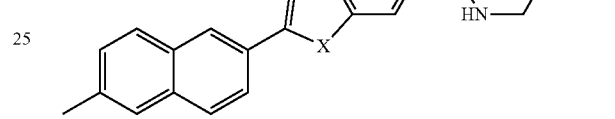

wherein X is S or O.

2. The two-photon fluorescent probe according to claim 1, which reacts with zinc ions, thereby generating fluorescence ranging from 400~650 nm.

3. A method for manufacturing a two-photon fluorescent probe represented by following Formula 1 by reacting a compound represented by following Formula 3 with a compound represented by following Formula 4 under nitrogen atmosphere:

[Formula 1]

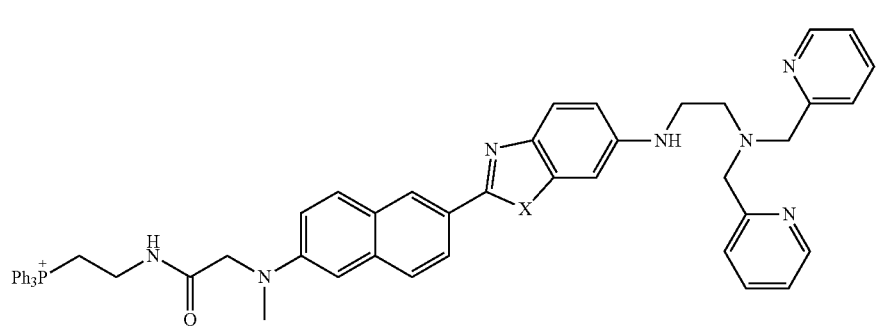

[Formula 3]

[Formula 4]

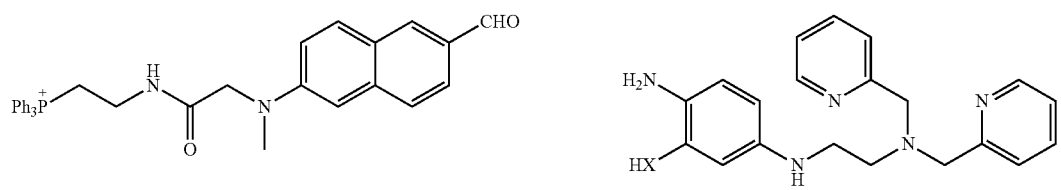

wherein X is S or O.

4. A method for manufacturing a two-photon fluorescent probe represented by following Formula 2 by reacting a compound represented by following Formula 5 with a compound represented by following Formula 6 under nitrogen atmosphere:

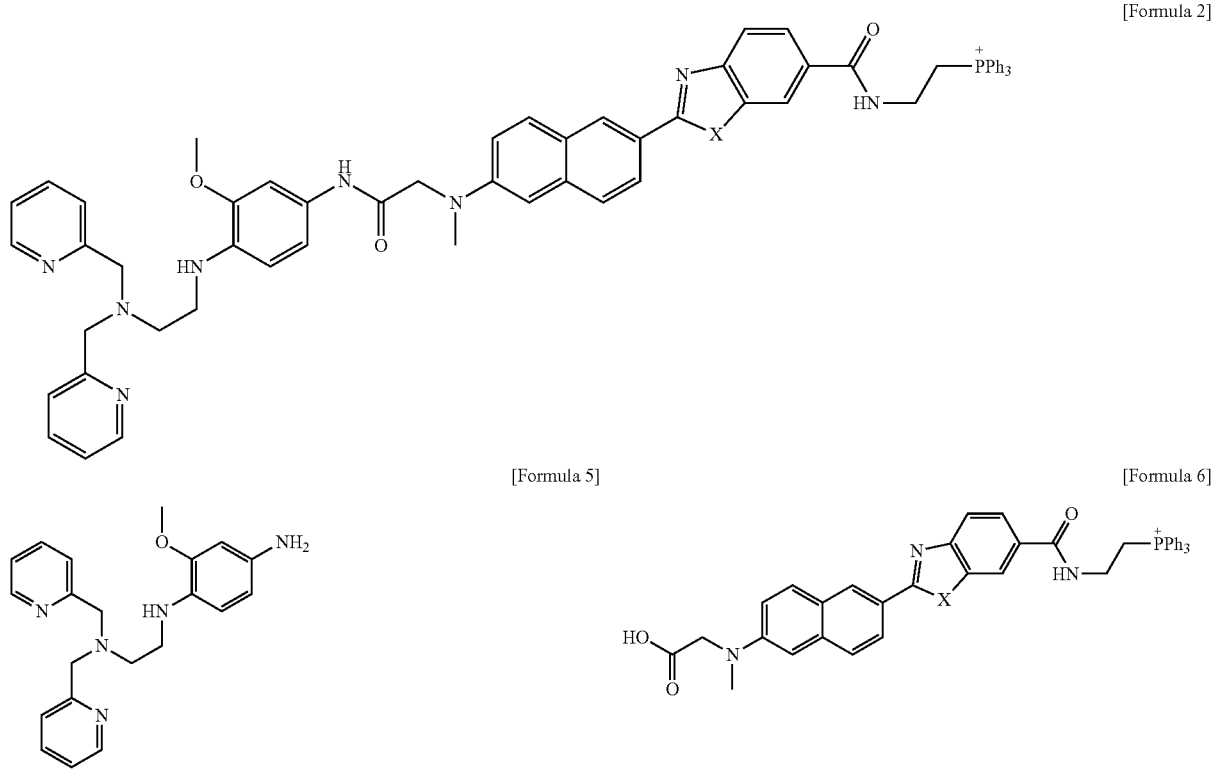

[Formula 2]

[Formula 5]

[Formula 6]

wherein X is S or O.

5. An imaging method of zinc ions present inside the mitochondria, comprising:
   (a) injecting the two-photon fluorescent probe according to claim 1 into cells;
   (b) reacting the two-photon fluorescent probe with zinc ions of the mitochondria, thereby generating fluorescence; and
   (c) observing the fluorescence with a two-photon microscope.

6. The imaging method according to claim 5, the fluorescence generated in step (b) is in the range from 400~650 nm.

* * * * *